United States Patent [19]

Schnur

[11] Patent Number: 5,387,584
[45] Date of Patent: Feb. 7, 1995

[54] BICYCLIC ANSAMYCINS
[75] Inventor: Rodney C. Schnur, Mystic, Conn.
[73] Assignee: Pfizer Inc., New York, N.Y.
[21] Appl. No.: 44,521
[22] Filed: Apr. 7, 1993
[51] Int. Cl.⁶ .................. A61K 31/415; C07D 487/06
[52] U.S. Cl. ...................................... 514/183; 540/461
[58] Field of Search ........................ 540/461; 514/183

[56] References Cited
U.S. PATENT DOCUMENTS
4,261,989 4/1981 Sasaki et al. ........................ 540/461

Primary Examiner—Robert T. Bond
Attorney, Agent, or Firm—Peter C. Richardson; Paul H. Ginsburg; Grover F. Fuller, Jr.

[57] ABSTRACT

This invention relates to compounds of the formula

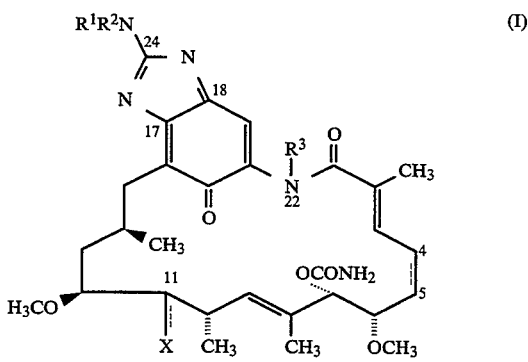

wherein $R^1$, $R^2$, $R^3$ and X are as defined below. Such compounds are useful as oncogene inhibitors and antitumor agents.

9 Claims, No Drawings

BICYCLIC ANSAMYCINS

This invention relates to novel bicyclic ansamycins pharmaceutical compositions comprising such compounds and the use of such compounds as oncogene product inhibitors and antitumor agents.

The bicyclic ansamycins of this invention are derivatives of the antibiotic geldanamycin, which is known to be useful against certain microorganisms, primarily yeast and fungi. Geldanamycin is referred to in U.S. Pat. No. 3,595,955. Semisynthetic derivatives of geldanamycin and their use as antitumor agents are described in Japanese Patent Application JP 88041885, which was published on Aug. 19, 1988, Japanese Patent Application JP 56100766, which was published on Aug. 12, 1981 and Japanese Patent Application JP 89002593, which was published on Jan. 18, 1989.

SUMMARY OF THE INVENTION

This invention relates to compounds of the formula

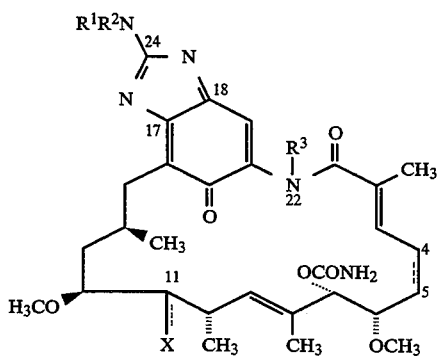

wherein the dotted lines between the carbon atoms at positions "4" and "5" and between X and the carbon at position "11" represent optional double bonds;

and wherein $R^1$ and $R^2$ are independently selected from hydrogen, $(C_1-C_8)$alkyl, $(C_1-C_8)$alkenyl, $(C_1-C_8)$alkynyl, $(C_3-C_7)$cycloalkyl and phenyl-$(C_1-C_3)$alkyl, wherein the phenyl moiety of said phenyl-$(C_1-C_3)$alkyl may optionally be substituted with from one to three substituents independently selected from halo, azido, nitro, $(C_1-C_6)$alkyl, $(C_1-C_6)$alkoxy, aryl, cyano and $NR^4R^5R^6$, wherein $R^4$, $R^5$ and $R^6$ are independently selected from hydrogen and $(C_1-C_6)$alkyl;

or $R^1$ and $R^2$ can form, together with the nitrogen to which they are attached, a heterocyclic ring selected from aziridine, azetidine, pyrrolidine, thiazolidine, oxazolidine, piperidine, morpholine, piperazine, 4-$(C_1-C_4)$alkylpiperidine, N-$(C_1C_1-C_6)$alkylpiperazine and N-benzylpiperazine;

$R^3$ is hydrogen or a group of the formula

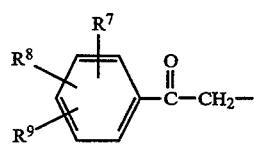

wherein $R^7$, $R^8$ and $R^9$ are independently selected from hydrogen, halo, azido, nitro, $(C_1-C_8)$alkyl, $(C_1-C_8)$alkoxy, aryl, cyano and $NR^{10}R^{11}R^{12}$ wherein $R^{10}$, $R^{11}$ and $R^{12}$ are independently selected from hydrogen and $(C_1-C_3)$alkyl;

X is halo or $OR^{13}$ when there is a single bond between X and the carbon at position "11", and X is oxo (=O) or oximino (=NOH) when there is a double bond between X and the carbon at position "11";

$R^{13}$ is selected from the group consisting of hydrogen, $R^{14}C(=O)$, $R^{14}SO_2$ and $R^{15}R^{16}NSO_2NHC(=O)$;

$R^{14}$ is selected from the group Consisting of hydrogen, $(C_1-C_8)$alkyl, amino$(C_1-C_8)$alkyl, hydroxy$(C_1-C_8)$alkyl and aryl, wherein said aryl is selected from phenyl and naphthyl, and wherein said aryl, $(C_1-C_8)$alkyl and the alkyl moieties of said amino$(C_1-C_8)$alkyl and hydroxy$(C_1-C_8)$alkyl may be substituted with one or more substituents, preferably with from zero to three substituents, independently selected from $(C_1-C_8)$alkyl, halo, amino, nitro, azido, hydroxy and $(C_1-C_8)$alkoxy; and $R^{15}$ and $R^{16}$ are independently selected from hydrogen, $(C_1-C_8)$alkyl, $(C_1-C_8)$alkenyl, $(C_3-C_7)$cycloalkyl, amino-$(C_1-C_8)$alkyl, hydroxy-$(C_1-C_8)$alkyl and methoxy-$(C_1C_8)$alkyl;

or $R^{15}$ and $R^{16}$ form, together with the nitrogen to which they are attached, a heterocyclic ring selected from aziridine, azetidine, pyrrolidine, thiazolidine, oxazolidine, piperidine, morpholine, piperazine, 4-$(C_1-C_4)$alkylpiperidine, N-$(C_1-C_6)$alkylpiperazine and N-benzylpiperazine.

The present invention also relates to the pharmaceutically acceptable acid addition salts of compounds of the formula I. The acids that may be used to prepare the pharmaceutically acceptable acid addition salts of the aforementioned base compounds of this invention are those that form non-toxic acid addition salts, i.e., salts containing pharmacologically acceptable anions, such as the hydrochloride, hydrobromide, hydroiodide, nitrate, sulfate or bisulfate, phosphate or acid phosphate, acetate, lactate, citrate or acid citrate, tartrate or bitartrate, succinate, maleate, fumarate, gluconate, saccharate, benzoate, methanesulfonate, ethanesulfonate, benzenesulfonate, p-toluene sulfonate and pamoate [i.e., 1,1'-methylene-bis-(2-hydroxy-3-naphthoate)]salts.

The term "halo", as used herein, unless otherwise indicated, includes chloro, fluoro, bromo and iodo.

The term "alkyl", as used herein, unless otherwise indicated, includes saturated monovalent hydrocarbon radicals having straight, branched or cyclic moieties or combinations thereof.

The term "one or more substituents," as used herein, includes from one to the maximum number of substituents possible based on the number of available bonding sites.

Compounds of the formula I wherein X is single bonded to the carbon at position "11" contain a chiral center at position "11". This invention relates to all stereoisomers of compounds of the formula I, including racemic mixtures thereof, that derive from the chirality of the carbon at position "11".

Preferred compounds of the formula I include those wherein: (a) each of $R^1$ and $R^2$ is methyl and X is hydroxy; (b) $R^1$ is methyl, $R^2$ is benzyl and X is hydroxy, or (c) $R^1$ and $R^2$, together with the nitrogen to which they are attached, form a 4-methylpiperidine ring, and X is hydroxy.

Examples of specific preferred compounds of the formula I are:

17-demethoxy-24-dimethylamino-17, 18-imidazo-geldanamycin;

17-demethoxy-24-(2'-hydroxymethylazetidine)-17, 18-imidazo-geldanamycin;

17-demethoxy-4,5-dihydro-24-dimethylamino-17, 18-imidazo-geldanamycin;

17-demethoxy-17, 18-imidazo-24-morpholine-geldanamycin;

24-amino-17-demethoxy-17, 18-imidazo-geldanamycin;

17-demethoxy-24-diethylamino-17, 18-imidazo-geldanamycin;

17-demethoxy-17, 18-imidazo-24-(4-methyl-piperidine)-geldanamycin;

24-benzylmethylamino-17-demethoxy-17, 18-imidazo-geldanamycin;

24-azetidine-17-demethoxy-17, 18-imidazo-geldanamycin;

11-acetyl-24-azetidine-17-demethoxy-17, 18-imidazo-geldanamycin; and 24-azetidine-17-demethoxy-4,5-dihydro-17, 18-imidazo-geldanamycin.

Other examples of compounds of the formula I are:

17-demethoxy-24-dimethylamino-11 -fluoro-17, 18-imidazo-geldanamycin;

11 -acetyl-17-demethoxy-24-dimethylamino-17, 18-imidazo-geldanamycin;

17-demethoxy-24-dimethylamino-17, 18-imidazo-11 -keto-geldanamycin;

17-demethoxy-22-(3',4'-dichlorophenacyl)-24-dimethylamino-17,18-imidazogeldanamycin;

11 -aminocarboxy-17-demethoxy-24-dimethylamino-17, 18-imidazo-geldanamycin;

17-demethoxy-4,5-dihydro-24-dimethylamino-11 -fluoro-17, 18-imidazogeldanamycin;

17-demethoxy-22-(3',4'-dichlorophenacyl)-4,5-dihydro-24-dimethylamino-17, 18-imidazo-geldanamycin;

17-demethoxy-24-dimethylamino-22-(4'-fluorophenacyl)-17, 18-imidazogeldanamycin;

17-demethoxy-24-dimethylamino-17, 18-imidazo-22-(3'-iodo-4'-azidophenacyl)geldanamycin;

17-demethoxy-22-(3',4'-dichlorophenacyl)-24-diethylamino-17,18-imidazogeldanamycin;

17-demethoxy-22-(3,4-dichlorophenacyl)-17, 18-imidazo-24-(4-methyl-piperidine)geldanamycin;

17-demethoxy-4,5-dihydro-17, 18-imidazo-24-(4'-methyl-piperidine)-geldanamycin;

17-demethoxy-4,5-dihydro-17, 18-imidazo-24-methylbenzylamino-geldanamycin;

and

11 -acetyl-17-demethoxy-17, 18-imidazo-24-methyl-benzylamino-geldanamycin.

This invention also relates to a pharmaceutical composition comprising an oncogene product inhibiting or an antitumor effective amount of a compound of the formula I, or a pharmaceutically acceptable salt thereof, and a pharmaceutically acceptable carrier.

This invention also relates to a method of inhibiting an oncogene product in a mammal, including a human, comprising administering to said mammal an oncogene product inhibiting effective amount of a compound of the formula I or a pharmaceutically acceptable salt thereof.

This invention also relates to a method of treating or preventing cancer in a mammal, including a human, comprising administering to said mammal an antitumor or oncogene product inhibiting effective amount of a compound of the formula 1 or a pharmaceutically acceptable salt thereof.

This invention also relates to a method of preventing or inhibiting the growth of a tumor in a mammal, including a human, comprising administering to said mammal an antitumor effective amount of a compound of the formula I or a pharmaceutically acceptable salt thereof.

DETAILED DESCRIPTION OF THE INVENTION

The preparation of compounds of the formula I is illustrated in the following reaction scheme and described below. In the reaction scheme and discussion that follow, $R^1$, $R^2$, $R^3$ and X, unless otherwise indicated, are defined as above.

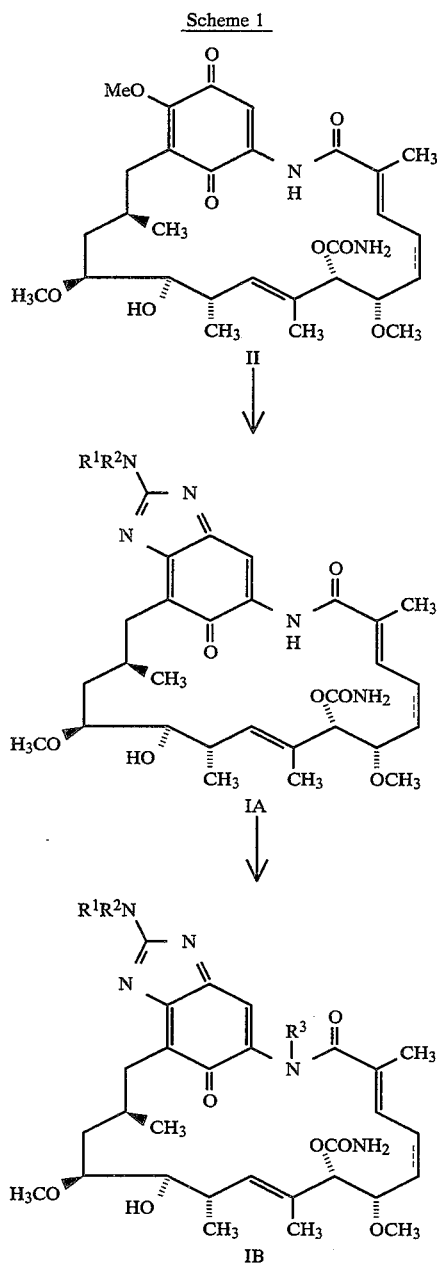

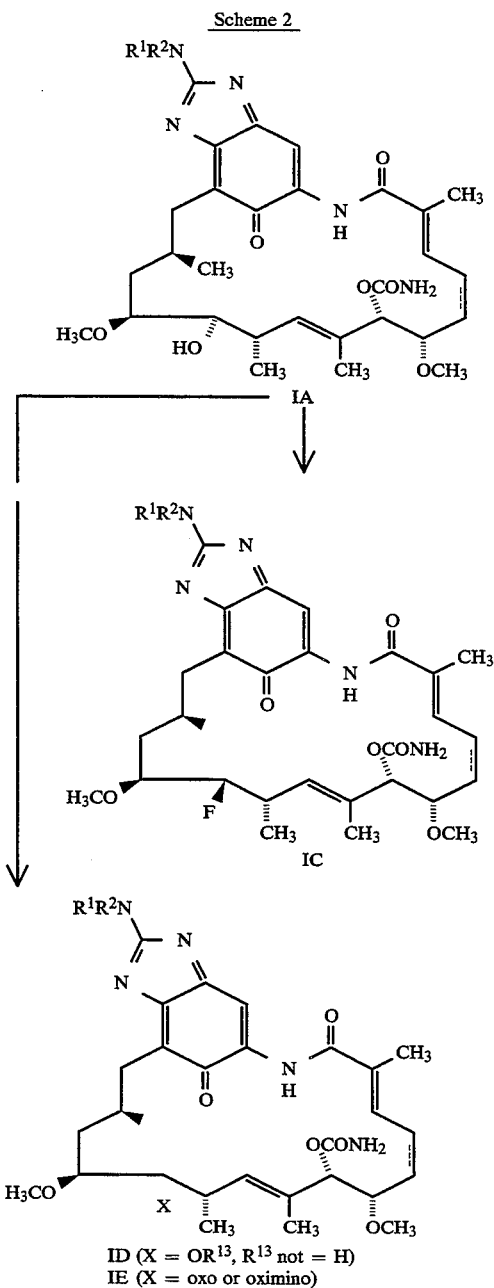

Scheme 2

ID (X = OR¹³, R¹³ not = H)
IE (X = oxo or oximino)

Scheme 1 above illustrates a method of preparing compounds of the formula I wherein $R^3$ is hydrogen and X is hydroxy. These compounds are hereinafter referred to as "compounds of the formula IA". Scheme 1 also illustrates the preparation of compounds of the formula I wherein $R^3$ is other than hydrogen and X is hydroxy. These compounds are hereinafter referred to (and depicted in Scheme 1) as "compounds of the formula 1B".

Referring to Scheme 1, the appropriate 1,1-disubstituted guanidinium salt, for example a hydrobromide, hydrochloride or sulfate (e.g. 1,1-dimethyl guanidine hydrochloride), is treated with a strong base such as sodium hydride or an alkoxide like potassium tert-butoxide in a polar aprotic solvent such as dimethylformamide (DMF), dimethylacetamide (DMAC) or N-methyl pyrrolidone (NMP), after which a compound of the formula II (which is geldanamycin when there is a double bond between the carbons at positions "4" and "5" and 4,5-dihydro-geldanamycin when there is a single bond between these carbons) is added to the reaction mixture. This reaction is typically conducted at a temperature from about 0° C. to about 40° C. for a period of about 1 hour to about 50 hours. Usually, it is sufficient and preferable, as a matter of convenience, for the reaction to be carried out at room temperature for about 24 hours.

The compounds of the formula IA produced by the above reaction can be alkylated at the nitrogen at position "22" to form the corresponding compounds of the formula I wherein X is hydroxy and $R^3$ is other than hydrogen. Such compounds are hereinafter referred to (and depicted in Scheme 1) as "compounds of the formula 1B". The alkylation is generally accomplished by treatment with base, such as lower alkoxide, in a polar solvent, for example, DMF, dimethylsulfoxide (DMSO), NMP or DMAC, followed by reaction with an appropriate alkylating agent such as a compound of the formula $R^3X$ wherein X is chloro, bromo or iodo. Reaction temperatures are usually maintained between 5° and 65° C., and are preferably between about 5°–25° C. Alternatively, such alkylations can be accomplished by reacting the compounds of formula IA with an alkyl halide of formula R3X in acetone with anhydrous potassium carbonate at the reflux temperature.

Scheme 2 illustrates the preparation of compounds of the formula I wherein $R^3$ is hydrogen and X is other than hydroxy from the corresponding compounds of the formula IA. Referring to Scheme 2, compounds of the formula IA can be converted into the corresponding compounds of the formula I wherein X is fluorine (hereinafter referred to and depicted in Scheme 2 as "compounds of the formula IC") by reacting them with diethylaminosulfurtrifluoride (DAST). This reaction is generally performed in an inert solvent (e.g., methylene chloride, chloroform or dichloroethane) at a temperature from about −78° to 0° C., preferably from about −78° to −50° C. Optimally, the reaction is quenched at low temperature with dilute aqueous base, for example 5% sodium bicarbonate. Other halogen derivatives of compounds of the formula IA, i.e., those derivatives wherein X is chloro, bromo or iodo, may be prepared by reacting the corresponding hydroxy compounds with a conventional halogenating agent (e.g., sulfuryl chloride, a boron trihalide, phosphorous tribromide or another phosphorous halide) using methods that are well known in the art.

Compounds of the formula IA can be converted into the corresponding compounds of the formula I that are acylated at position "11" (i.e., compounds wherein $R^3$ is hydrogen and X is OR13 but not hydroxy, hereinafter referred to and depicted in Scheme 2 as "compounds of the formula ID") by acylation with the appropriate anhydride, acid chloride or isocyanate, for example, chlorosulfonyl isocyanate, in the presence of a nonnucleophilic base. Solvents suitable for use in these reactions include a wide variety of aprotic polar and nonpolar media, for example acetone, chloroform, ethyl acetate, dimethylformamide (DMF), pyridine, tetrahydrofuran. Bases that may be used include 1,8-diazabicyclo[5.4.0]undec-7-ene (DBU), triethylamine and 4-dimethylaminopyridine.

Additionally, compounds of the formula IA can be converted into the corresponding compounds of the formula I wherein $R^3$ is hydrogen and X is oxo or oximo (hereinafter referred to and depicted in Scheme 2 as "compounds of the formula IE") as follows. The oxo derivatives may be prepared by treating the compounds of formula IA with a standard oxidizing reagent such as pyridinium chlorochromate, pyridinium dichromate, oxalyl chloride/dimethylsulfoxide, Dess-Martin periodinane or Jones reagent in inert solvent such as methylene chloride, chloroform or acetone, at temperatures ranging from about $-60°$ C. to about $100°$ C. These oxidations are preferably carried out with Dess-Martin periodinane in chloroform at reflux. The resulting ketones may be converted to the corresponding oximes by treating them with hydroxylamine hydrochloride in the presence of base (e.g. sodium acetate, pyridine, sodium carbonate, sodium hydroxide, potassium carbonate or triethylamine) in water or a lower alcohol solvent at a temperature from about $0°$ C. to about $100°$ C. Preferably, the oxime is formed at room temperature in ethanol with triethylamine.

The compounds of the formula I that are basic in nature are capable of forming a wide variety of different salts with various inorganic and organic acids. Although such salts must be pharmaceutically acceptable for administration to mammals, it is often desirable in practice to initially isolate a compound of the formula I from the reaction mixture as a pharmaceutically acceptable salt and then simply convert the latter back to the free base compound by treatment with an alkaline reagent, and subsequently convert the free base to a pharmaceutically acceptable acid addition salt. The acid additions salts of the base compounds of this invention are readily prepared by treating the base compound with a substantially equivalent amount of the chosen mineral or organic acid in an aqueous solvent medium or in a suitable organic solvent such as methanol or ethanol. Upon careful evaporation of the solvent, the desired solid salt is obtained.

The preparation of other compounds of the formula I not specifically described above can be accomplished using combinations of the above reactions that will be clear to those skilled in the art in view of the foregoing disclosure.

The compounds of formula I and their pharmaceutically acceptable salts are useful as antitumor agents (including, but not limited to anticancer agents) and oncogene product inhibitors. They are useful, for example, in inhibiting the ErbB-2, src and abl oncogene products. They are also useful in inhibiting certain growth factors that play an important role in uncontrolled cell proliferation such as the epidermal growth factor (EGF) receptor, the nerve growth factor (NGF) receptor, the platelet derived growth factor (PDGF) receptor and the insulin receptor.

The ability of compounds of the formula I to inhibit the ErbB-2 oncogene product may be determined by the following method for determining the p185 concentrations in SKBr3 cells.

SKBr3 human breast cancer cells, obtained from the ATTC, Rockville, Md. were seeded in 8 well tissue culture plates (9.5 $cm^2$/well, Falcon, Becton Dickenson, Uncoln Park, N.J.) at $5 \times 10^5$ cells/well in 2 ml McCoys medium, supplemented with 10% fetal calf serum and glutamine. Cells were allowed to attach overnight at $37°$ C. in a 5% $CO_2$ atmosphere.

The compounds are dissolved in DMSO and tested over a range of concentrations by addition to the medium, followed by incubation at $37°$ C. for 6 hours. At the end of the incubation, the medium is aspirated from the well, and the cells are washed twice with 2 ml of TNK buffer (50 mM tris (hydroxymethyl)aminomethane HCl, 140 mM NaCl, 3.3 mM KCl, 0.5 mM sodium orthovanadate, adjusted to pH 7.4). The cells are then lysed by addition of 250 $\mu$l boiling Laemmli sample buffer (140 mM tris(hydroxymethyl)aminomethane HCl, pH 6.8, 5.7% sodium dodecyl sulfate, 29% glycerol) with shaking. The cell lysate is transferred to a tube and then placed in a boiling water bath for 5 mins. The lysates are then sonicated with a probe sonicator and stored at $-70°$ C. until analysis.

The p185 concentration of each sample may be determined by standard immunoblotting procedures essentially as described by Harlow and Lane (*Antibodies: A Laboratory Manual,* Cold Spring Harbor Laboratory, 1988). A standard portion of each sample is mixed with dithiothreitol (10% added of a 1M solution), and then a portion corresponding to $\sim 10$ $\mu$g of protein is blotted onto a nitrocellulose membrane (BA-S, Schleicher and Schuell, Keene, N.H.) equilibrated with rinse buffer (10 mM Tris HCl pH 7.4, 150 mM NaCl) by use of a dot blot apparatus (Mini-fold, Schleicher and Schuell, Keene, N.H.) with an underlayer of filter paper. The wells are rinsed with 200 $\mu$l of a rinse buffer, blocked by incubation with a blocking buffer (5% bovine serum albumin, 1% ovalbumin in rinse buffer), and then incubated for 4 to 12 hours with a 1:1000 dilution of NT1, an affinity purified rabbit polyclonal antibody raised by standard methods (Harlow and Lane, *Antibodies, A Laboratory Manual,* Cold Spring Harbor Laboratory, 1988) against a peptide representing the C-terminal domain of human p185 (sequence, TAENPEYLGLDVPV, by the standard 1 letter amino acid code). The membrane is then rinsed twice for 10 minutes with rinse buffer and once for 10 minutes in rinse buffer with 0.05% Triton X-100, and then twice more for 10 minutes in rinse buffer. The membrane is then incubated with a 1:3000 dilution of horseradish peroxidase labeled donkey anti-rabbit antibody (Amersham, Arlington Heights, Ill.) in a rinse buffer with shaking for 20–45 minutes. The membrane is then again rinsed twice for 10 minutes in the rinse buffer, once for 10 minutes in the rinse buffer with 0.05% Triton X-100, and then twice more for 10 minutes in the rinse buffer. The p 185 is then visualized with the ECL Detection Kit (Amersham, Arlington Heights, Ill.) and recorded with Hyperfilm-ECL (Amersham, Arlington Heights, Ill.). The p185 is then estimated by densitometric analysis of the film. $IC_{50}$ values are determined by reference to the p185 content of samples of cells exposed only to vehicle (DMSO) and measured as described.

The ability of compounds of the formula I to inhibit the ErbB-2 oncogene product may also be determined by the method of Kamps et al., *Oncogene,* 2, 305–315 (1988) for determining the phosphorylation of p185 in SKBR3 and other ErbB-2 transformed cell lines.

The ability of compounds of the formula I and their pharmaceutically acceptable salts to inhibit the growth of certain human carcinoma cells may be determined by the methods of Alley et al., *Cancer Research.,* 48, 589–601 (1988) using SKBr3 and MCF7, cell lines. This reference is incorporated herein in its entirety.

When the compounds of the formula I and their pharmaceutically acceptable salts are used as antiproliferative agents, such as anticancer agents, they can be administered to a mammalian subject, including a human subject, either alone, or, preferably, in combination with pharmaceutically-acceptable carriers or diluents in a pharmaceutical composition according to standard pharmaceutical practice. The compounds can be administered orally or parenterally. Parenteral administration includes intravenous, intramuscular, intraperitoneal, subcutaneous and topical administration.

For oral use of a compound of formula I or a pharmaceutically acceptable salt thereof, the compound can be administered, for example, in the form of tablets or capsules, or as an aqueous solution or suspension. In the case of tablets for oral use, carriers which are commonly used include lactose and corn starch, and lubricating agents, such as magnesium stearate, are commonly added. For oral administration in capsule form, useful diluents are lactose and dried corn starch. When aqueous suspensions are required for oral use, the active ingredient is combined with emulsifying and suspending agents. If desired, certain sweetening and/or flavoring agents can be added. For intramuscular, intraperitoneal, subcutaneous and intravenous use, sterile solutions of the active ingredient are usually prepared, and the pH of the solutions should be suitably adjusted and buffered. For intravenous use, the total concentration of solutes should be controlled to render the preparation isotonic.

In a pharmaceutical composition comprising a compound of formula I or a pharmaceutically acceptable salt thereof, the weight ratio of carrier to active ingredient will normally be in the range from 1:10 to 10:1. However, in any given case, the ratio chosen will depend on such factors as the solubility of the active component, the dosage contemplated and the precise route of administration.

When a compound of the formula I or a pharmaceutically acceptable salt thereof is used in a human subject, the daily dosage will normally be determined by the prescribing physician. Moreover, the dosage will vary according to the age, weight and response of the individual patient, as well as the severity of the patient's symptoms and the potency of the particular compound being administered. However, the effective dose in most instances will be 0.01 to 1.0 g as needed (e.g., every four to six hours). For chronic administration, in most instances an effective dose will be from 0.01 to 1.0 g per day in single or divided doses. On the other hand, it may be necessary to use dosages outside these limits in some cases.

This invention is illustrated by, but not limited to the details of the following examples.

EXAMPLE 1

17-Demethoxy-24-dimethylamino-17, 18-imidazo-geldanamycin 1,1-Dimethylguanidinium sulfate (Aldrich, 0.7314 g, 2.676 mmol) was ground to a fine powder with mortar and pestle, added to a flame dried flask under nitrogen and slurried in 10 mL dimethylformamide. Potassium tert-butoxide (Aldrich, 0.600 g, 5.35 mmol) was added and the reaction was stirred at room temperature for 10 minutes. Geldanamycin (0.500 g, 0.892 mmol) was added and the reaction immediately turned purple. The reaction was stirred overnight and the color changed from purple to dark green. The reaction was diluted with 100 mL ethyl acetate and washed with 0.36 mL acetic acid in 50 mL water, followed by brine (3×50 mL), and water (2×50 mL). The organic layer was dried over magnesium sulfate, filtered, and evaporated to dryness. The green residue was purified by flash column chromatography on 400 g of silica gel using 3% methanol/97% chloroform as eluent to afford a green residue which was dissolved in a minimal amount of chloroform and precipitated with hexane, filtered and dried in vacuo; 0.384 g, (72%), m.p. 231° C. (dec).

$^1$H-NMR (CDCl$_3$) δ0.86 (d, J=5 Hz, 6H, 10-Me and 14-Me), 1.47–1,81 (br m, 3H, H-13, H-14), 1.72 (s, 3H, 8-Me), 1.96 (s, 3H, 2-Me), 2.24–2.46 (br m, 2H, H-15), 2.70 (m, 1H, H-10), 3.21 (s, 3H, OMe), 3.25 (s, 3H, OMe), 3.32 (s, 3H, 24-N-Me), 3.35–3.52 (m, 1H, H-12), 3.42 (s, 3H, 24-N-Me), 3.55 (m, 1H, H-11), 4.25 (d, J=9 Hz, 1H, H-6), 4.56–4.79 (br m, 2H, NH$_2$), 5.10 (s, 1H, H-7), 5.76 (br m, 2H, H-5, H-9), 6.50 (t, J=9 Hz, 1 H, H-4), 6.85 (d, J=9 Hz, 1H, H-3), 7.48 (s, 1 H, H-19), 8.92 (s, 1H, H-22).

Mass spectrum: m/z 622.3 (M$^+$+Na).

IR (CHCl$_3$, cm$^{-1}$): 1730, 1675, 1580.

Calc'd for C$_{31}$H$_{43}$N$_5$O$_7$·0.5 H$_2$O: C, 61.37; H, 7.30; N, 11.55. Found: C, 61.63; H, 6.45; N, 10.62.

Unless otherwise indicated, the title compounds of Examples 2–11 were prepared by the method of Example 1 starting with the appropriate guanidinium salt and the appropriate geldanamycin.

EXAMPLE 2

17-Demethoxy-24-(2'-hydroxymethylazetidine)-17, 18-imidazo-geldanamycin

The title compound was obtained by the method of Example 1 starting with 1-amidino-2'-hydroxymethyl-azetidine (Giannis et al, Angew. Chem. Int. Ed., 28, 218 (1989)) and geldanamycin and was purified by flash column chromatography using 200 g silica gel eluting with 5% methanol/95% chloroform. The green residue was dissolved in a minimal amount of chloroform and precipitated with hexane, filtered and dried in vacuo; 0.539 g, (24%), m.p. 214° C. (dec).

$^1$H-NMR (CDCl$_3$) δ0.92 (d, J=7 Hz, 6H, 10-Me, 14-Me), 1.39–1.73 (br m, 3H, H-13, H-14), 1.76 (s, 3H, 8-Me), 1.98 (s, 3H, 2-Me), 2.18 (m, 1H, H-15), 2.28–2.51 (br m, 3'CH$_2$), 2.71 (m, 1H, H-15), 3.14–3.38 (br m, 2H, H-10, H-12), 3.22 (s, 3OMe), 3.27 (s, 3H, OMe), 3.45 (m, 1H, H-11 ), 3.70 (m, 1H, azetidine CH), 3.94 (br m, 1H, azetidine CH), 4.25 (d, J=8 Hz, 1H, H-6), 4.3–5.0 (br m, 5H, NH$_2$ and azetidine CH, CH$_2$), 5.09 (s, 1H, H-7), 5.78 (m, 2H, H-5, H-9), 6.49 (t, J=8 Hz, 1H, H-4), 6.85 (d, J=8Hz, 1H, H-3), 7.49 (s, 1H, H-19 ), 8.95 (s, 1H, H-22).

Mass spectrum: m/z 664 (M+Na+H).

IR (KBr, cm$^{-1}$): 1735, 1705, 1675, 1640, 1620, 1585.

Calc'd for C$_{33}$H$_{45}$N$_5$O$_8$·2.5 H$_2$O: C, 57.88; H, 7.35; N, 10.22. Found: C, 57.89; H, 6.70; N, 9.92.

EXAMPLE 3

17-Demethoxy-4,5-dihydro-24-dimethylamino-17, 18-imidazo-geldanamycin

The title compound was prepared from the guanidine of Example 1 and 4,5-dihydrogeldanamycin; 0.32 g, (15%) m.p. 208° C. (dec).

$^1$H-NMR (CDCl$_3$) δ0.93 (d, J=6 Hz, 6H, 10-Me, 14-Me), 1.57–1.76 (br m, 5H, H-5, H-13, H-14), 1.61 (s, 3H, 8-Me), 1.83 (s, 3H, 2-Me), 2.22–2.43 (br m, 4H, H-4, H-15), 2.69 (t, J=6 Hz, 1H, H-10), 2.99 (d, J=5 Hz, 1H, 11-OH), 3.21–3.45 (m, 2H, H-6, H-12), 3.28 (s, 3H, OMe), 3.31 (s, 3H, 24-Me), 3.33 (s, 3H, OMe), 3.42 (s, 3H, 24-Me), 3.52 (m, 1H, H-11), 4.62 (br s, 2H, NH$_2$), 5.09 (d, J=5 Hz, 1H, H-7), 5.68 (d, J=7 Hz, 1H, H-9), 6.14 (t, J=5 Hz, 1H, H-3), 7.32 (s, 1H, H-19), 8.99 (s, 1H, NH-22).

Mass spectrum: m/z 624 (M+ +Na), 602 (M+).
IR (KBr, cm$^{-1}$): 1730, 1695, 1635, 1618, 1585.
Calc'd for C$_{31}$H$_{45}$N$_5$O$_7$·H$_2$O: C, 60.27; H, 7.67; N, 11.34. Found: C, 60.71; H, 7.23; N, 10.99.

EXAMPLE 4

17-Demethoxy-17, 18-imidazo-24-morpholine-geldanamycin

1-Amidino-morpholine hydrobromide (Pfaltz & Bauer, 0.45 g, 2.14 mmol) was ground to a fine powder with mortar and pestle and added to a flame dried flask under nitrogen and slurried in 5 ml dimethylformamide. Potassium tert-butoxide (Aldrich, 0.24 g, 2.14 mmol) was added and the reaction was stirred at room temperature for 10 minutes. Geldanamycin (0.200 g, 0.3567 mmol) was added and the reaction immediately turned purple. The reaction was stirred overnight and the color changed from purple to dark green. The reaction was diluted with 100 mL ethyl acetate and washed with 0.356 mL acetic acid in 50 ml water, followed by brine (3×50 mL) and water (2×50 mL). The organic layer was dried over magnesium sulfate, filtered and evaporated to dryness. The green residue was dissolved in a minimal amount of chloroform and precipitated with hexane, filtered and dried in vacuo; 0.45 g, (19%) m.p. 235° C. (dec).

$^1$H-NMR (CDCl$_3$) δ0.89 (d, J=7 Hz, 6H, 10-Me, 14-Me), 1.55–1.79 (br m, 3H, H-13, H-14), 1.63 (s, 3H, 8-Me), 1.92 (s, 3H, 2-Me), 2.19–2.43 (br m, 2H, H-15), 2.69 (m, 1H, H-10), 3.21(s, 3H, OMe), 3.22–3.38 (br m, 1H, H-12), 3.42 (m, 1H, H-11), (br m, 8H, morpholine CH$_2$), 4.23 (d, J=8 Hz, 1H, H-6), 4.65 (br s, 2H, NH$_2$), 5.08 (s, 1H, H-7), 5.78 (m, 2H, H-5, H-9), 6.49 (t, J=8 Hz, 1H, H-4), 6.85 (d, J=8 Hz, 1H, H-3), 7.48 (s, 1H, H-19 ), 8.95 (s, 1H, H-22).

Mass spectrum: m/z 664 (M+ +Na+H).
IR (KBr, cm$^{-1}$): 1735, 1705, 1675, 1640, 1620, 1585.
Calc'd for C$_{33}$H$_{45}$N$_5$O$_8$·0.5 H$_2$O: C, 61.10; H, 6.99; N, 10.79. Found: C, 61.19; H, 6.98; N, 10.36.

EXAMPLE 5

24-Amino-17-demethoxy-17, 18-imidazo-geldanamycin

Sodium Hydride (Aldrich, 0.051 g, 2.14 mmol) was washed with hexane (2×5 mL) and dried in a three neck flask that was flame dried and equipped with nitrogen. Dimethylformamide (5 mL) was syringed into flask and guanidine hydrochloride (Aldrich, 0.204 g, 2.14 mmol) was added and the reaction stirred at room temperature for ten minutes. Geldanamycin (0.200 g, 0.3567 mmol) was added and the reaction immediately turned purple. The reaction was stirred for 36 hours, diluted with 100 mL of ethyl acetate, and washed with water (3×50 mL) containing 0.146 mL of acetic acid and then washed with brine (3×50 mL). The organic layer was dried over magnesium sulfate, filtered and evaporated to a gray/blue solid, 0.85 g (42%), m.p. >270° C.

$^1$H-NMR (C$_6$D$_5$N) δ0.79 (m, 6H, 10-Me, 14-Me),1.42 (m, 1H), 1.64–1.85 (br m, 2H), 1.72 (s, 3H, 8-Me), 1.74 (s, 3H, 2-Me), 2.04 (m, 1H, H-10), 2.22 (m, 1H, H-15), 2.46 (m, 1H, H-15), 2.83 (s, 3H, OMe), 2.93 (s, 3H, OMe), 3.15 (m, 1H, H-12), 3.59 (m, 1H, H-11), 4.42 (m, 1H, H-6), 5.32 (s, 1H, H-7), 5.71 (m, 1H, H-5), 5.95 (m, 1H, H-9), 6.12 (t, J=8 Hz, 1H, H-4), 7.03 (m, 1H, H-3), 7.61 (m, 1H, H-19), 9.31 (br s, 1H, H-22).

Mass spectrum: m/z 594.3 (M+ +Na+H).
IR ( KBr, cm$^{-1}$): 1735, 1705, 1690, 1640, 1610, 1570.

Calc'd for C$_{29}$H$_{39}$N$_5$O$_7$·H$_2$O: C, 59.27; H, 6.69; N, 11.92. Found: C, 59.64; H, 6.43; N, 11.31.

EXAMPLE 6

17-Demethoxy-24-diethylamino-17,18-imidazo-geldanamycin

The title compound was obtained by following Example 5 using 1,1 diethylguanidinium sulfate (Pant et al., *Z. Pysiolgishe Chemie,* 335, 272 (1964)); 0.12 g, (5%), m.p. 225° C. (dec).

$^1$H-NMR (CDCl$_3$) δ0.79 (m, 6H, 10-Me, 14-Me), 1.10 (m, 6H, β-CH$_3$), 1.42 (m, 1H), 1.53–1.73 (br m, 2H), 1.59 (s, 3H, 8-Me), 1.83 (s, 3H, 2-Me), 2.24 (m, 2H, H-15), 2.56 (m, 1H, H-10), 3.08 (s, 3H, OMe), 3.14–3.27 (br m, 2H, 11-OH, H-12), 3.15 (s, 3H), OMe), 3.35 (m, 1H, H-11), 3.48–3.41 (br m, 4H, α-CH$_2$), 4.11(d, J=8 Hz, 1H, H-6, 4.46–4.72 (br m, 2H, NH2), 4.98 (s, 1H, H-7), 5.65 (m, 2H, H-5, H-9), 6.36 (t, J=8 Hz, 1H, H-4), 6.72 (d, J=8 Hz, 1H, H-3), 7.35 (s, 1H, H-19), 8.86 (s, 1H, H-22).

Mass spectrum: m/z 650 (M+ +Na+H).
IR (CH$_2$Cl$_2$, cm$^{-1}$): 1735, 1680, 1620, 1565.
Calc'd for C$_{33}$H$_{48}$N$_5$O$_7$·0.25 H$_2$O: C, 62.88; H, 7.59; N, 11.11. Found: C, 62.90; H, 7.03; N, 9.95.

EXAMPLE 7

17-Demethoxy-17,18-imidazo-24-(4-methyl-piperidine )-geldanamycin

2-Methyl-2-thiopseudourea sulfate (Aldrich, 10 g, 0.72 mol) and 4-methyl piperidine (Aldrich, 11.4 g, 0.11 mol), were dissolved in 35 mL of water and heated on a steam bath for 5 hours. After cooling overnight the reaction mixture was evaporated to an oil, dissolved into a minimal amount of methanol, passed through charcoal and evaporated to a solid, 5.2 gm (25%), m.p. 278° C. (dec). This was used to prepare the title compound by the method of Example 1; 0.098 g, (38%), m.p. 190° C. (dec).

$^1$H-NMR (CDCl$_3$) δ0.92 (m, 6H, 10-Me, 14-Me), 1.20–1.41 (br m, 3H, 4'CH$_3$), 1.60–1.84 ( br m, 3H, H-13, H-14), 1.72 (s, 3H, 8-Me), 1.93 (s, 3H, 2-Me), 2.35 (m, 2H, H-15), 2.71 (m, 1H, H-10), 3.05–3.27 (br m, 5H, H-12 and β-CH$_2$), 3.21 (s, 3H, OMe), 3.28 (s, 3H, OMe), 3.28–3.4 (m, 1H, H-12), 3.50 (m, 1H, H-11), 3.53–3.72 (m, 1H, γ-CH), 4.25 ( d, J=8 Hz, 1H, H-6), 4.55–4.86 (br m, 4H, α-CH$_2$), 5.10 (s, 1H, H-7), 5.78) m, 2H, H-5, H-9 ), 6.50 (t, J=8 Hz, 1H, H-4), 6.86 (d, J=8 Hz, 1H, H-3), 7.47 (s, 1H, H-19), 9.00 (s, 1H, H-22).

Mass spectrum: m/z 676 (M+ +2H).
IR (KBr, cm$^{-1}$): 1735, 1705, 1675, 1635, 1615, 1570.
Calc'd for C$_{35}$H$_{49}$N$_5$O$_7$·0.75 H$_2$O: C, 63.19; H, 7.65; N, 10.53. Found: C, 63.20; H, 7.30; N, 10.11.

EXAMPLE 8

24-Benzyl-17-demethoxy-17, 18-imidazo-24-methyl-geldanamycin

1-Benzyl-1-methyl guanidinium sulfate (Aldrich, 0.45 g, 1.07 mmol) was added to a flame dried flask under nitrogen containing 5 mL of anhydrous dimethylformamide. Potassium tert-butoxide (Aldrich, 0.24 g, 2.14 mmol) was added and the reaction was stirred at room temperature for 10 min. Geldanamycin (0.200 g, 0.357 mmol) was added and the reaction immediately turned purple. The reaction was stirred overnight and the color changed from purple to dark green. The reaction was refluxed two hours then cooled to room temperature, diluted with 100 mL ethyl acetate and washed with water (2×50 mL). The organic layer was dried over magnesium sulfate, filtered, and evaporated to dryness. The green residue was purified by flash column chromatography on 60 gm of silica gel with 3% methanol/97% chloroform to afford a green residue. The green residue was dissolved in a minimal amount of chloroform, precipitated with hexane, filtered and dried in vacuo; 0.028 gm, (11%), m.p. 190° C. (dec).

$^1$H-NMR (CDCl$_3$) δ indicated two rotomers 0.091 (m, 6H, 10-Me, 14-Me), 1.59-1.84 (br m, 3H, H-13, H-14), 1.72 (s, 3H, 8-Me), 1.96 (s, 3H, 2-Me), 2.26-2.49 (br m, 2H, H-15), 2.71 (m, 1H, H-10), 3.21 (s, 3H, OMe), 3.25-3.70 (br m, 2H, H-11, H-12), 3.31 (s, 3H, OMe), 3.33 (s, 3H, 24N-CH$_3$), 4.23 (d, J=8 Hz, 1H, H-6), 4.61–4.81 (br m, 2H, NH$_2$), 4.97 (ABq, J=14 Hz, J=40 Hz, 2H, 24-N-CH$_2$), 4.86 (ABq, J=14 Hz, J=58 Hz, 2H, 24-N-CH$_2$), 5.11 (s, 1H, H-7), 5.81 (m, 2H, H-5, H-9), 6.50 (t, J=8 Hz, 1H, H-4), 6.87 (d, J=8 Hz, 1H, H-3), 7.13-7.36 (br m, 5H, aromatic), 7.48, 7.52 (pr s, 1H, H-19), 8.94 (s, 1H, H-22).

Mass spectrum: m/z 698 (M+ +Na+2H).
IR (KBr, cm$^{-1}$): 1735, 1705, 1675, 1635, 1620, 1575.
Calc'd for C$_{37}$H$_{47}$N$_5$O$_7$: C, 65.95; H, 7.03; N, 10.39. Found: C, 66.26; H, 7.31; N, 9.93.

EXAMPLE 9

24-Azetidine-17, 18-imidazo-17-demethoxy-geldanamycin

1-Amidino-azetidine was prepared by reaction of 3,5 dimethylpyrazole-1-carboxamidine (Aldrich, 0.704 g, 3.50 mmol) in 7 mL isoamyl alcohol with azetidine (0.20 g 3.5 mmol). After stirring at room temperature for 7 days, the reaction mixture was evaporated to a cream colored solid. The solid was washed with diethyl ether (3×25 mL) dried in vacuo; 0.491 g (86%), m.p. 155°-157° C. New title compound was obtained by the method of Example 1; 0.048 gm, (22%), m.p. 230° C. (dec).

$^1$H-NMR (CDCl$_3$) δ0.91 (m, 6H, 10-Me, 14-Me), 1.49-1.78 (br m, 2H, H-13, H-14), 1.72 (s, 3H, 8-Me), 1.98 (s, 3H, 2-Me), 2.24-2.53 (br m, 3H, H-15 and β-azetidine CH$_2$), 2.71 (m, 1H, H-10), 3.21 (s, 3H, OMe),3.27-3.36 (m, 1H, H-12), 3.29 (s, 3H, OMe), 3.45 (m, 1H, H-11 ), 4.23 (d, J=8 Hz, 1H, H-6),4.37–4.61 (br m, 4H, CH$_2$ azetidine), 4.7 (m, 2H, NH$_2$), 5.08 (s, 1H, H-7), 5.80 (m, 2H, H-5, H-9), 6.51 (t, J=8 Hz, 1H, H-4)), 6.82 (d, J=8 Hz, 1H, H-3), 7.47 (s, 1H, H-19), 8.94 (s, 1H, NH-22);

Mass spectrum: m/z 633 (M+ +Na).
IR (KBr, cm$^{-1}$): 1735, 1705, 1675, 1635, 1620, 1580.
Calc'd for C$_{32}$H$_{43}$N$_5$O$_7$·5.5 H$_2$O: C, 54.22; H, 7.67; N, 9.89. Found: C, 54.01; H, 6.09; N, 9.39.

EXAMPLE 10

11-Acetyl-24-azetidine-17-demethoxy-17,18-imidazo-geldanamycin

The product of Example 9 (0.100 g, 0 164 mmol) was acetylated by treatment with acetic anhydride (0.033 g, 0.328 mmol, 0.030 mL) 4-dimethylaminopyridine (0.020 g, 0.164 mmol) and triethylamine (0.050 g, 0.492 mmol, 0.069 mL) at room temperature in 3 mL of methylene chloride for 24 hours. An additional equivalent each of acetic anhydride and triethylamine were added and stirring was continued for 54 hours. The reaction was poured into 150 mL of water and extracted with 2×150 mL of ethyl acetate. The combined organic layers were washed with 3×100 mL of water, dried with magnesium sulfate, filtered and evaporated in vacuo to a green residue. This was dissolved in 2 mL of chloroform and precipitated with hexanes to give a solid after filtration and drying in vacuo; 0.043 g, (40%), m.p. 179°-81° C.

$^1$H-NMR (CDCl$_3$) δ0.86 (d, J=6 Hz, 3H, 10- Me), 1.05 (d, J=6 Hz, 3H, 14-Me), 1.45-1.8 (br m, 3H, H-5, H-13, H-13, H-14), 1.69 (s, 3H, 8-Me), 1.84 (s, 3 H, 2-Me), 1.95 (s, 3H, acetyl 0H3), 2.20 (m, 1H, H-15), 2.34 (m, 1H, H-15), 2.46 (pent, 1H, azetidine CH$_2$), 2.90 (m, 1H, H-10), 3.25 (s, 3H, OMe), 3.33-3.4 (br m, 1H, H-12), 3.34 (s, 3H, OMe), 4.17 (m, 1H, H-11), 4.35 (d, J=8 Hz, 1H, H-6), 4.40 (t, J=8 Hz, azetidine CH$_2$), 4.51 (t, J=8 Hz, azetidine CH$_2$), 4.6-5.0 (br m, 2H, NH$_2$), 4.84 (m, 1H, H-9), 5.02 (s, 1H, H-7), 5.74 (t, J=9 Hz, 1H, H-5), 6.50 (t, J=9 Hz, 1H, H-4), 7.35 (m, 1H, H-3), 7.38 (br s, 1H, H-19), 8.95 (br s,1H, H-22).

Mass spectrum: m/z 676 (M+ +Na+2H).
Calc'd for C$_{34}$H$_{45}$N$_5$O$_8$·H$_2$O; C, 60.97; H, 7.07; N, 10.46. Found: C, 61.35; H, 6.71;N, 10.29.

EXAMPLE 11

24-Azetidine-17-demethoxy-4,5-dihydro-17, 18-imidazo-geldanamycin

The title compound was prepared by the method of Example 1 from 1-amidinoazetidine hydrochloride and 4,5-dihydrogeldanamycin.

0.062 g, (29%), m.p. 190° C. (dec).

$^1$H-NMR (CDCl$_3$) δ1.05 (d,J=6 Hz, 6H, 10-Me and 14-Me), 1.72-1.93 (br m, 6H, H-5, H-13, H-14), 1.83 (s, 3H, 8-Me), 2.01 (s, 3H, 2-Me), 2.37-2.70 (m, 6H, H-4, H-15, azetidine-CH$_2$), 2.86 (m, 1H, H-10), 3.05 (m, 1H, 11-OH), 3.38-3.55 (br m, 2H, H- 12), 3.44 (s, 3H, OMe), 3.50 (s, 3H, OMe), 3.69 (m, 1H, H-11 ), 4.52–4.91 (br m, 6H, CH$_2$ azetidine, NH$_2$), 5.27 (d, J=3 Hz, 1H, H-7), 5.83 (d, J=8 Hz, 1H, H-9), 6.31 (m, 1H, H-3), 7.51 (br s, 1H, H-19), 9.14 (br s,1 H, H-22).

Mass spectrum: m/z 636 (M+Na+2H).
IR (KBr, cm$^{-1}$): 1725, 1695, 1615, 1575.

I claim:
1. A compound of the formula

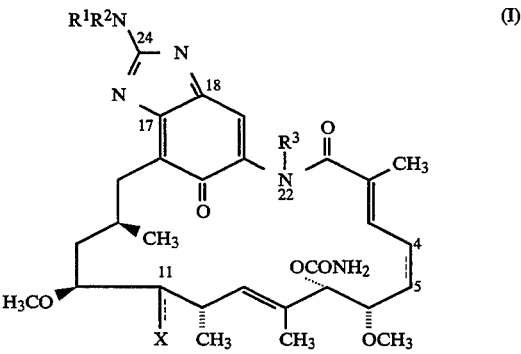

wherein the dotted lines between the carbon atoms at positions "4" and "5" and between X and the carbon at position "11" represent optional double bonds;

and wherein R$^1$ and R$^2$ are independently selected from hydrogen, (C$_1$-C$_3$)alkyl, (C$_1$-C$_8$)alkenyl, (C$_1$-C$_8$)alkynyl, (C$_3$-C$_7$)cycloalkyl, and phenyl-(C$_1$-C$_3$)alkyl, wherein the phenyl moiety of said phenyl-(C$_1$-C$_3$)alkyl may optionally be substituted with from one to three substituents independently selected from halo, azido, nitro, (C$_1$-C$_6$)alkyl, ($C_1$–$C_6$)alkoxy, aryl, cyano and $NR^4R^5R^6$, wherein $R^4$, $R^5$ and $R^6$ are independently selected from hydrogen and ($C_1$–$C_6$)alkyl;

or $R^1$ and $R^2$ can form, together with the nitrogen to which they are attached, a heterocyclic ring selected from aziridine, azetidine, pyrrolidine, thiazolidine, oxazolidine, piperidine, morpholine, piperazine, 4-($C_1$–$C_4$)alkylpiperidine, N-($C_1$–$C_6$)alkylpiperazine and N-benzylpiperazine;

$R^3$ is hydrogen or a group of the formula

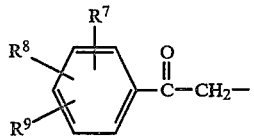

wherein $R^7$, $R^8$ and $R^9$ are independently selected from hydrogen, halo, azido, nitro, ($C_1$–$C_8$)alkyl, ($C_1$–$C_8$)alkoxy, aryl, cyano and $NR^{10}R^{11}R^{12}$ wherein $R^{10}$, $R^{11}$ and $R^{12}$ are independently selected from hydrogen and ($C_1$–$C_3$)alkyl;

X is halo or $OR^{13}$ when there is a single bond between X and the carbon at position "11", and X is oxo (=O) or oximino (=NOH) when there is a double bond between X and the carbon at position "11";

$R^{13}$ is selected from the group consisting of hydrogen, $R^{14}C(=O)$, $R^{14}SO_2$ and $R^{15}R^{16}NSO_2NHC(=O)$;

$R^{14}$ is selected from the group consisting of hydrogen, ($C_1$–$C_8$)alkyl, amino($C_1$–$C_8$)alkyl, hydroxy($C_1$–$C_8$)alkyl and aryl, wherein said aryl is selected from phenyl and naphthyl, and wherein said aryl, ($C_1$–$C_8$)alkyl and the alkyl moieties of said amino($C_1$–$C_8$)alkyl and hydroxy($C_1$–$C_8$)alkyl may be substituted with one or more substituents, preferably with from zero to three substituents, independently selected from ($C_1$–$C_8$)alkyl, halo, amino, nitro, azido, hydroxy and ($C_1$–$C_8$)alkoxy; and $R^{15}$ and $R^{16}$ are independently selected from hydrogen, ($C_1$–$C_8$)alkyl, ($C_1$–$C_8$)alkenyl, ($C_3$–$C_7$)cycloalkyl, amino-($C_1$–$C_8$)alkyl, hydroxy-($C_1$–$C_8$)alkyl and methoxy-($C_1$–$C_8$)alkyl;

or $R^{15}$ and $R^{16}$ form, together with the nitrogen to which they are attached, a heterocyclic ring selected from aziridine, azetidine, pyrrolidine, thiazolidine, oxazolidine, piperidine, morpholine, piperazine, 4-($C_1$–$C_4$)alkylpiperidine, N-($C_1$–$C_6$)alkylpiperazine and N-benzylpiperazine;

or a pharmaceutically acceptable salt thereof.

2. A compound according to claim 1 wherein: (a) each of $R^1$ and $R^2$ is methyl and X is hydroxy; (b) $R^1$ is methyl, $R^2$ is benzyl and X is hydroxy, or (c) $R^1$ and $R^2$, together with the nitrogen to which they are attached, form a 4-methylpiperidine ring, and X is hydroxy.

3. A compound according to claim 1, wherein said compound is selected from the group consisting of:
   17-demethoxy-24-dimethylamino-17, 18-imidazo-geldanamycin;
   17-demethoxy-24-(2'-hydroxymethylazetidine)-17,18-imidazo-geldanamycin;
   17-demethoxy-4,5-dihydro-24-dimethylamino-17, 18-imidazo-geldanamycin;
   17-demethoxy-17,18-imidazo-24-morpholine-geldanamycin;
   24-amino-17-demethoxy-17,18-imidazo-geldanamycin;
   17-demethoxy-24-diethylamino-17, 18-imidazo-geldanamycin;
   17-demethoxy-17, 18-imidazo-24-(4-methylpiperidine)-geldanamycin;
   24-benzylmethylamino-17-demethoxy-17, 18-imidazo-geldanamycin;
   24-azetidine-17-demethoxy-17, 18-imidazo-geldanamycin;
   11-acetyl-24-azetidine-17-demethoxy-17, 18-imidazo-geldanamycin; and
   24-azetidine-17-demethoxy-4,5-dihydro-17,18-imidazo-geldanamycin.

4. A pharmaceutical composition comprising an oncogene product inhibiting or an antitumor effective amount of a compound according to claim 1 and a pharmaceutically acceptable carrier.

5. A method of inhibiting an oncogene product in a mammal comprising administering to said mammal an oncogene inhibiting effective amount of a compound according to claim 1.

6. A method according to claim 5 of inhibiting the ErbB-2 oncogene product.

7. A method of treating or preventing cancer in a mammal comprising administering to said mammal an oncogene product inhibiting or antitumor effective amount of a compound according to claim 1.

8. A method according to claim 6, wherein the cancer is human breast, ovarian or pancreatic cancer.

9. A method of preventing or inhibiting the growth of a tumor in a mammal, comprising administering to said mammal an antitumor effective amount of a compound according to claim 1.

* * * * *